United States Patent [19]
Stern et al.

[11] Patent Number: 5,902,757
[45] Date of Patent: May 11, 1999

[54] STITCH BONDED FABRIC AND FLUID-RETAINING FABRIC MADE THEREWITH

[75] Inventors: Randolph A. Stern, Cincinnati, Ohio; Michael N. Byles, Jamestown, N.C.

[73] Assignee: Standard Textile Co., Inc., Cincinnati, Ohio

[21] Appl. No.: 08/858,211

[22] Filed: May 10, 1997

[51] Int. Cl.$^6$ .................................................. D04H 1/08
[52] U.S. Cl. ..................... 442/324; 442/326; 442/36; 442/38; 442/57; 428/102; 428/192; 604/378; 604/383
[58] Field of Search ................... 442/36, 38, 57, 442/324, 326; 428/102, 192; 604/378, 383; 66/190, 191, 192

[56] References Cited

U.S. PATENT DOCUMENTS

| | | |
|---|---|---|
| 1,816,416 | 7/1931 | Willingham . |
| 2,580,089 | 12/1951 | Grant . |
| 2,672,673 | 3/1954 | Shaw . |
| 4,026,129 | 5/1977 | Sternlieb . |
| 4,128,686 | 12/1978 | Kyle et al. . |
| 4,144,612 | 3/1979 | Yamaguchi . |
| 4,181,514 | 1/1980 | Lefkowitz et al. . |
| 4,675,226 | 6/1987 | Ott ........................................... 428/102 |
| 4,811,573 | 3/1989 | Sternlieb .................................. 66/193 |
| 4,876,128 | 10/1989 | Zafiroglu .............................. 112/262.1 |
| 5,330,817 | 7/1994 | Arnott et al. ............................. 428/85 |
| 5,356,402 | 10/1994 | Gillies et al. ........................... 604/375 |
| 5,365,677 | 11/1994 | Dahlgren .................................. 36/3 A |

FOREIGN PATENT DOCUMENTS

| | | |
|---|---|---|
| 261904 | 3/1988 | European Pat. Off. . |
| 429802 | 6/1991 | European Pat. Off. . |
| 496567 | 7/1992 | European Pat. Off. . |

OTHER PUBLICATIONS

*The Machine of the Malipol Type* (undated).
*International Search Report*, PCT/US98/09353, mailed Aug. 31, 1998 (4 pages).

*Primary Examiner*—Christopher Raimund
*Attorney, Agent, or Firm*—Wood, Herron & Evans, L.L.P.

[57] ABSTRACT

A stitch bonded fabric sheet (10) has a felt web (12) with hydrophobic layer (14) and a hydrophilic layer (16) stitch bonded with yarns (18) to create yarn faces (24 and 26) over the respective outer surfaces (20 and 22) of the felt web (12). Sheet (10) may be used as a fluid-retention fabric such as to replace the facing fabric and felt layer in an incontinent pad.

29 Claims, 2 Drawing Sheets

STITCH BONDED FABRIC AND FLUID-RETAINING FABRIC MADE THEREWITH

BACKGROUND OF THE INVENTION

I. Field of the Invention

The present invention relates to stitch bonded fabrics, and more particularly, to such fabrics used as fluid-retaining fabrics such as in incontinent products.

II. Description of Prior Art

Various incontinent pads have been employed such as in hospital settings to retain fluids expelled from the body while also protecting the bed linens therebelow. To this end, a typical incontinent pad has a knit or woven facing fabric layer to which is quilted a felt layer. The facing fabric layer provides a soft, comfortable layer against the patient's skin, and cooperates with the felt layer to hold the large volume of fluid that may be expelled from the patient. The felt layer further provides rigidity to the pad so that it does not crumple up and become uncomfortable under the weight of the patient.

A barrier layer, typically of vinyl or polyurethane with an outer tricot fabric layer, is attached to the felt such as by being stitched to the edge of the quilted layers or by being bonded to the felt with adhesive. To provide for better patient comfort, it is desirable to wick fluids away from the topside of the facing fabric so as to maintain as dry a surface as possible. To this end, one highly desirable facing fabric developed and marketed by Standard Textile Co., Inc., under the mark Comply® is an integral web fabric that provides a hydrophobic upper surface and a hydrophilic lower surface in wicking communication with the upper surface. With that fabric, fluids are wicked away from the face of the fabric and into the hydrophilic, fluid-absorbing lower portion where the fluids may be retained.

While incontinent pads have enjoyed wide-spread success, the manufacture of such pads presents significant cost concerns, especially due to the need to separately manufacture the facing fabric and the felt layer, and to then apply the quilting process to hold those layers together.

SUMMARY OF THE INVENTION

The present invention provides an improved fluid-retaining fabric such as may be substituted for the facing fabric and felt of the prior incontinent pads and which reduces the costs of manufacture thereof. To this end, and in accordance with principles of the present invention, the fabric of the present invention is provided by stitch bonding a felt web having a hydrophobic upper aspect and a hydrophilic lower aspect, with stitch bonding yarns which in a single process holds the felt web aspects together and also defines top and bottom yarn faces of the fabric formed with the stitch bonding yarns, with the top yarn face presenting the patient comfort surface, and the bottom yarn face providing a surface for adhesive connection to a barrier layer without interfering with either the structural rigidity or absorbency provided by the felt web.

The stitch-bonded fabric of the present invention may be utilized as a fluid-retaining fabric and may be incorporated into an incontinent pad such as by the attachment of a barrier layer to the bottom yarn face.

By virtue of the foregoing, there is thus provided an improved facing fabric that incorporates the advantageous features of a felt layer without the added cost of separate manufacture of the facing fabric and the felt, and without the cost of the still-further quilting process.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

DETAILED DESCRIPTION OF THE DRAWINGS

Figure 1:
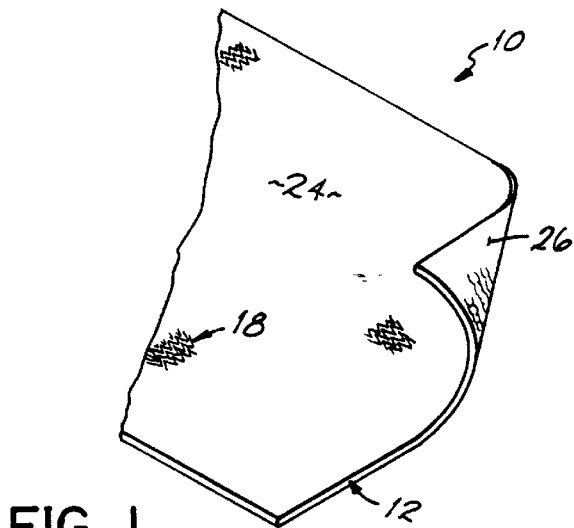
FIG. 1 is a perspective view of one embodiment of a sheet of stitch bonded fabric in accordance with the principles of the present invention.

With reference to FIGS. 1–4, there is shown one embodiment of a sheet 10 of stitch bonded fabric constructed in accordance with the principles of the present invention. Sheet 10 includes a central felt web 12 having an upper layer or aspect 14 of hydrophobic felt and a lower layer or aspect 16 of hydrophilic felt so as to be fluid retaining relative to upper aspect 14. Layer 14 may be composed of polyester and/or polypropylene and layer 16 may be composed of rayon. Layers 14 and 16 are secured together by a plurality of stitch bonding threads or yarns 18. Felt layers 14, 16 may be two separate, but adjacent layers or may be needle punched together into a single, integral web. In either case, web 12 presents an upper surface 20 defined by the upper side of the first layer 14, and a lower surface 22 defined by the lower side of the second layer 16. The properties of web 12 are such that fluid presented to layer 14 will wick down into layer 16 where it may be retained.

Stitch bonding yarns 18 repeatedly extend through felt web 12 with a plurality of yarn segments 18' extending over or across the upper surface 20 of web 12, and a plurality of yarn segments 18" extending over or across lower surface 22 of web 12. It will be appreciated that yarn segments 18' and 18" do not become embedded into the web 12 below surfaces 20 or 22 thereof, but rather extend across the surfaces 20 and 22, and are of sufficient density that yarn segments 18' cooperate to define a top yarn face 24 of fabric 10 above web upper surface 20, and yarn segments 18" cooperate to define a bottom yarn face 26 of fabric 10 below web lower surface 22. Faces 24 and 26 are effectively continuous such that web 12 is not exposed thereat, although small gaps or interstices (as at 28) between adjacent yarn segments 18' or 18" may allow viewing of felt surface 20 or 22 upon close inspection. It will be noted that FIGS. 3 and 4 are greatly exaggerated to show interstices 28 in faces 24 and 26.

Figure 3:
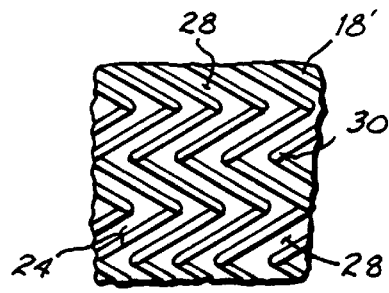
FIG. 3 is a close-up, top elevational view of the fabric of FIG. 1.
Figure 4:
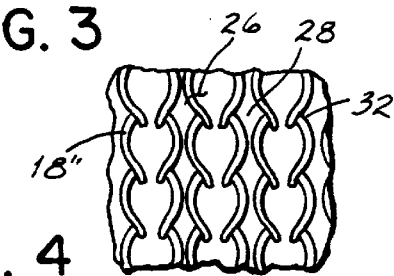
FIG. 4 is a close-up, bottom elevational view of the fabric of FIG. 1.
Figure 2:
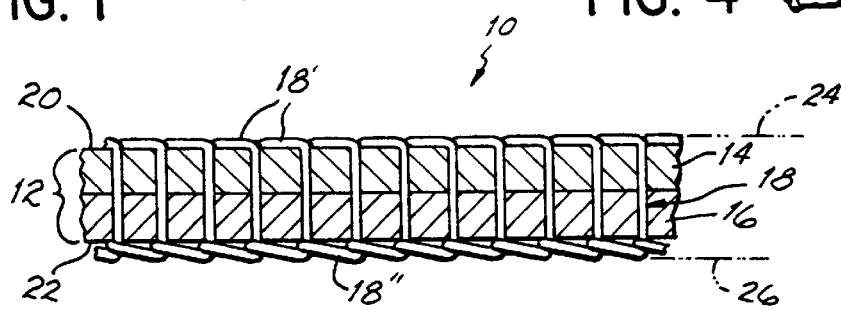
FIG. 2 is a diagrammatic, partially broken away, cross-sectional view taken along line 2—2 of the fabric of FIG. 1.

Yarns 18 are knitted in a flat stitch construction across the web upper surface 20 such that yarn segments 18' form underlaps as at 30 in FIG. 3. Yarn segments 18", on the other hand, form overlaps as at 32 in FIG. 4. The underlaps 30 and overlaps 32 are the result of the usual knit construction provided by stitch bonding such as with existing Malipol-type machines as are known in the art. With such machines, sheet 10 is formed such that top yarn face 24 is at the technical back and bottom yarn face 26 is at the technical face during the knitting process. Yarn 18 may be hydrophobic on hydrophilic, the former assisting in wicking fluid down into lower layer 16 of felt web 12. Yarns 18 may be continuous polymeric filaments of hydrophobic material such as polyester or may be spun yarns of natural hydrophilic material such as cotton, or may be a blend of polymeric and natural materials.

Figure 5:
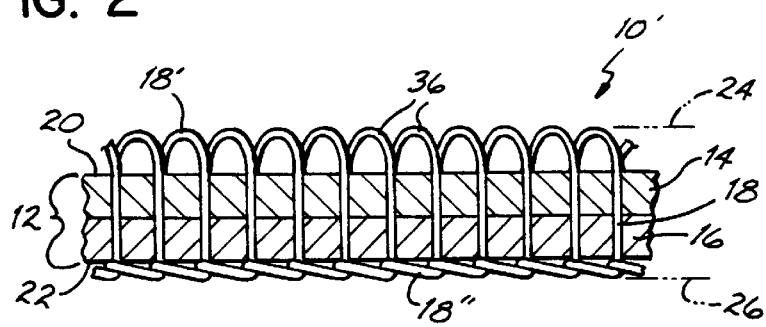
FIG. 5 is a view like FIG. 2 showing an alternative embodiment of a stitch bonded fabric in accordance with the principles of the present invention.

With reference to FIG. 5, an alternative embodiment of stitch bonded fabric 10' is constructed like fabric 10 but with yarns 18 being stitched in a loop knit construction across web upper surface 20 such that yarn segments 18' also define a plurality of loops 36 in the top yarn face 24.

Figure 6:
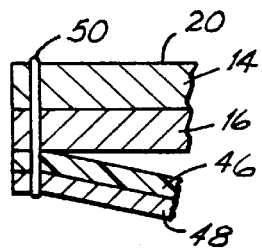
FIG. 6 is a partial cross-sectional view of edge stitching of an incontinent pad incorporating the fabric sheet of FIG. 1.
Figure 7:
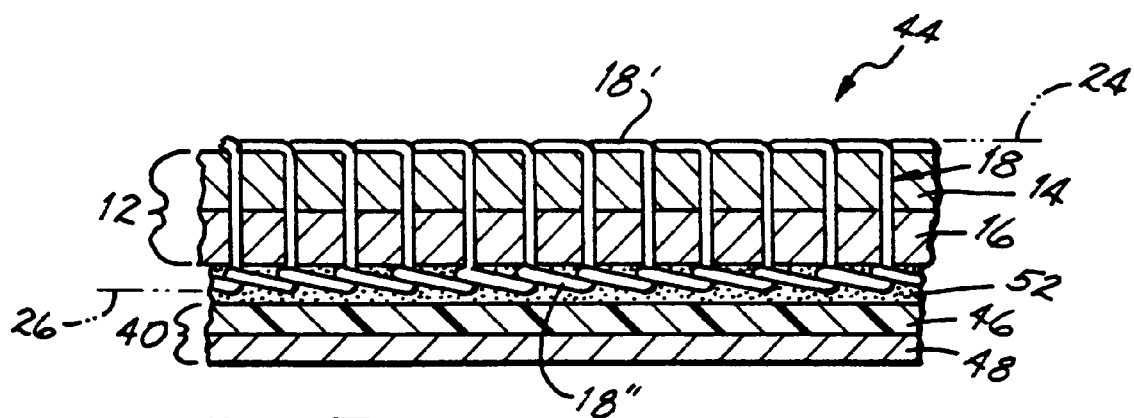
FIG. 7 is a cross-sectional, diagrammatic view of an incontinent pad incorporating the fabric sheet of FIG. 1.

In use, sheet 18 (or 18') may function as a fluid-retaining fabric such that fluid (not shown) at face 24 will pass into web 12 and be wicked from layer 14 into layer 16 of web 12 whereat the fluid is retained. To this end, a barrier layer 40 may be attached to bottom yarn face 26 of the sheet to thus define an incontinent pad 44 or the like as shown in FIGS. 6 and 7. Barrier layer 40 may include a fluid barrier ply 46 such as vinyl or polyurethane. Additionally, layer 40 may include a tricot ply 48 to provide a fabric outer layer to pad 44. Barrier ply 46 may be attached to yarn face 26 by edge-stitching 50 to sheet 18 or may be attached directly to yarn segments 18" of yarn bottom face 26. Alternatively, barrier ply 46 may be adhesively applied to face 26 such as with an adhesive lamination layer 52, depending upon the materials involved and the performance characteristics of the barrier layer 40.

Figure 8:
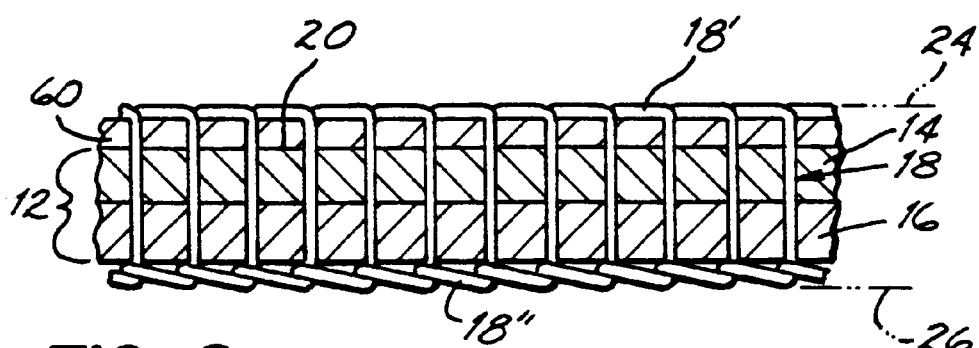
FIG. 8 is a view like FIG. 2 showing the sheet of FIG. 1 with an interposed scrim layer.

By virtue of the foregoing, there is thus provided a combined facing fabric and felt such as for incontinent products that may be made in one process step to thereby reduce the cost of manufacture thereof While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. For example, one or more additional layers such as a hydrophobic scrim 60 (FIG. 8) of remay material may be interposed over (or under) web 12 such as between surface 20 and yarn segments 18' (and/or between surface 22 and yarn segments 18") to provide a protective layer to prevent the non-woven fibers (not shown) of felt web 12 from projecting through yarn face 24 (or 26) created by the stitch bonding yarns 18' (or 18"). The invention in its broader aspects is, therefore, not limited to the specific details, representative apparatus and method, and illustrative examples shown and described. Accordingly, departures may be made from such details without departing from the spirit or scope of the general inventive concept.

Having described the invention, what is claimed is:

1. A stitch bonded facing fabric comprising:
   a first layer of hydrophobic felt;
   a second layer of hydrophilic felt being adjacent to the first layer so as to define a felt web having an upper surface defined by an upper side of the first layer and a lower surface defined by a lower side of the second layer; and
   a plurality of stitch bonding yarns repeatedly extending through the felt web with yarn segments extending across both the upper and lower surfaces of the felt web such that the yarn segments extending across the felt web upper surface cooperate to form a top yarn face above the felt web upper surface and the yarn segments extending across the felt web lower surface cooperate to form a bottom yarn face below the felt web lower surface.

2. The stitch bonded fabric of claim 1 further comprising a scrim layer interposed between one of the surfaces of the felt web and the yarn segments extending thereacross.

3. The facing fabric of claim 1 wherein the yarn segments extending across the felt web upper surface form underlaps.

4. The facing fabric of claim 3 wherein the yarn segments extending across the felt web lower surface form overlaps.

5. The facing fabric of claim 1 wherein the yarn segments extending across the felt web lower surface form overlaps.

6. The facing fabric of claim 1 wherein the yarns are stitched in a flat stitch construction across the felt web upper surface.

7. The facing fabric of claim 1 wherein the yarns are stitched in a loop knit construction across the felt web upper surface to define a plurality of yarn loops in the top yarn face.

8. The facing fabric of claim 1 wherein the yarns are hydrophobic.

9. The facing fabric of claim 1 wherein the yarns are hydrophilic.

10. The facing fabric of claim 1 wherein the yarns are continuous filaments.

11. The facing fabric of claim 1 wherein the yarns are spun yarn.

12. A stitch bonded facing fabric comprising:
    a felt web having a hydrophobic upper aspect extending from an upper surface of the web and a hydrophilic lower aspect extending from a lower surface of the web; and
    a plurality of stitch bonding yarns repeatedly extending through the felt web with yarn segments extending across both the upper and lower surfaces of the felt web such that the yarn segments extending across the felt web upper surface cooperate to form a top yarn face above the felt web upper surface and the yarn segments extending across the felt web lower surface cooperate to form a bottom yarn face below the felt web lower surface.

13. The stitch bonded fabric of claim 12 further comprising a scrim layer interposed between one of the surfaces of the felt web and the yarn segments extending thereacross.

14. The facing fabric of claim 12 wherein the yarn segments extending across the felt web upper surface form underlaps.

15. The facing fabric of claim 14 wherein the yarn segments extending across the felt web lower surface form overlaps.

16. The facing fabric of claim 12 wherein the yarn segments extending across the felt web lower surface form overlaps.

17. The facing fabric of claim 12 wherein the yarns are stitched in a flat stitch construction across the felt web upper surface.

18. The facing fabric of claim 12 wherein the yarns are stitched in a loop knit construction across the felt web upper surface to define a plurality of yarn loops in the fabric top.

19. The facing fabric of claim 12 wherein the yarns are hydrophobic.

20. The facing fabric of claim 12 wherein the yarns are hydrophilic.

21. The facing fabric of claim 12 wherein the yarns are continuous filaments.

22. The facing fabric of claim 12 wherein the yarns are spun yarn.

23. A fluid-retaining fabric comprising:

a stitch bonded facing fabric having a first layer of hydrophobic felt, a second layer of hydrophilic felt being adjacent to the first layer so as to define a felt web having an upper surface defined by an upper side of the first layer and a lower surface defined by a lower side of the second layer, and a plurality of stitch bonding yarns repeatedly extending through the felt web with yarn segments extending across both the upper and lower surfaces of the felt web such that the yarn segments extending across the felt web upper surface cooperate to form a top yarn face above the felt web upper surface and the yarn segments extending across the felt web lower surface cooperate to form a bottom yarn face below the felt web lower surface; and a barrier layer attached to the bottom yarn face.

24. The fluid-retaining fabric of claim 23 further comprising adhesive attaching the barrier layer to the bottom yarn face.

25. The fluid-retaining fabric of claim 23 wherein the first and second felt layers are needle punched into a single felt web.

26. The fluid-retaining fabric of claim 23 wherein the barrier layer includes a fluid barrier ply and a fabric ply.

27. The fluid-retaining fabric of claim 26 wherein the barrier ply is attached to the bottom yarn face.

28. The fluid-retaining fabric of claim 23 wherein the barrier layer includes a fluid barrier ply.

29. The fluid-retaining fabric of claim 23 further comprising edge stitching attaching the barrier layer to the bottom yarn face.

* * * * *